US006284947B1

(12) United States Patent
Gordon-Kamm et al.

(10) Patent No.: US 6,284,947 B1
(45) Date of Patent: Sep. 4, 2001

(54) METHODS OF USING VIRAL REPLICASE POLYNUCLEOTIDES AND POLYPEPTIDES

(75) Inventors: William J. Gordon-Kamm, Urbandale; Keith S. Lowe, Johnston; Matthew A. Bailey, Des Moines; Carolyn A. Gregory, Clive; George J. Hoerster, Des Moines, all of IA (US); Brian A. Larkins; Brian R. Dilkes, both of Tucson, AZ (US); Ronald Burnett, Bethlehem, PA (US); Young Min Woo, Tucson, AZ (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/257,131

(22) Filed: Feb. 25, 1999

(51) Int. Cl.[7] .............................. C12N 5/04; C12N 15/33; C12N 15/82; C12N 15/90; A01H 1/00
(52) U.S. Cl. ...................... 800/290; 435/417; 435/419; 435/320.1; 435/411; 435/412; 435/415; 435/416; 435/468; 800/278; 800/287; 800/288; 800/298; 800/312; 800/314; 800/317.2; 800/317.4; 800/320; 800/320.1; 800/320.2; 800/320.3; 800/322
(58) Field of Search ................................ 435/69.1, 320.1, 435/410, 411, 412, 415, 416, 417, 419, 468; 536/23.72; 800/278, 287, 288, 290, 295, 298, 312, 314, 317.2, 317.4, 320, 320.1, 320.2, 320.3, 322

(56) References Cited

FOREIGN PATENT DOCUMENTS

| WO 91/13542 | 9/1991 | (WO) | A01H/5/00 |
|---|---|---|---|
| WO 97/47745 | 12/1997 | (WO) | C12N/15/29 |
| WO 98/56811 | 12/1998 | (WO) | C07K/14/00 |
| WO 99/66055 | 12/1999 | (WO) | C12N/15/82 |

OTHER PUBLICATIONS

Xie Q., et al., (1996), *EMBO Journal*, 15(18): 4900–4908, "Plant cells contain a novel member of the retinoblastoma family of growth regulatory proteins".
Collins S., et al., (1996), *Virology*, 219: 324–329, "The Two Nonstructural Proteins from Wheat Dwarf Virus Involved in Viral Gene Expression and Replication Are Retinoblastoma–Binding Proteins".
Gutierrez C. (1998), *Current Opinion in Plant Biology*, 1: 492–497, "The retinoblastoma pathway in plant cell cycle and development".
Schalk et al., "Wheat dwarf virus, a geminivirus of graminaceous plants needs splicing for replication", *The EMBO Journal*, 8(2):359–364 (1989).
Hanley–Bowdoin et al., "Expression of functional replication protein from tomato golden mosaic virus transgenic tobacco plants" *Proc. Natl. Acad. Sci. USA*, 87:1446–1450 (1990).
Graffi et al, Proc. Natl. Acad. Sci., USA, vol.93, pp. 8962–8967, 1996.*
Nagar et al, Plant Cell, vol. 7, pp. 705–719, 1995.*
Chasan, R., "Geminiviruses: A Twin Approach to Replication", *The Plant Cell*, 2:659–660; 1995.
Davies et al., "The Structure, Expression, Functions and Possible Exploitation of Geminivirus Genomes", *Plant DNA Infectious Agents*/edited by T. Hohn and J. Schell, Wien:Springer–Verlag, 2:31–52; 1987.
Stanley, J., "Geminiviruses: plant viral vectors", *Current Opinion in Genetics and Development*, 3:91–96; 1993.
Timmermans et al., "Geminiviruses and Their Uses as Extrachromosomal Replicons", *Annual Review Plant Physiol. Plant Mol. Biol*, 45:79–112; 1994.
Orozco, B.M., "Functional Domains of a Geminivirus Replication Protein", *The Journal of Biological Chemistry*, 272(15):9840–9846; 1997.
Xie Q., "Identification and Analysis of a retinoblastoma binding motif in the replication protein of a plant DNA virus: requirement for efficient viral DNA replication", *The EMBO Journal*, 14(16):4073–4082; 1995.
Gutierrez, C., "The retinoblastoma pathway in plant cell cycle and development", *Current Opinion in Plant Biology*, 1:492–497; 1998.

* cited by examiner

*Primary Examiner*—Amy J. Nelson
*Assistant Examiner*—Ashwin D. Mehta
(74) *Attorney, Agent, or Firm*—Pioneer Hi-Bred International, Inc.

(57) ABSTRACT

The invention provides novel methods of using viral replicase polypeptides and polynucleotides. Included are methods for increasing transformation frequencies, increasing crop yield, providing a positive growth advantage, modulating cell division, transiently modulating cell division, and for providing a means of positive selection.

20 Claims, 3 Drawing Sheets

(2 of 3 Drawing Sheet(s) Filed in Color)

METHODS OF USING VIRAL REPLICASE POLYNUCLEOTIDES AND POLYPEPTIDES

TECHNICAL FIELD

The present invention relates generally to plant molecular biology.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion and secondary growth.

A complex network controls cell proliferation in eukaryotes. Various regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions.

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems.

In addition, many differentiated cells have the potential to both dedifferentiate and to reenter the cell cycle. The study of plant cell cycle control genes is expected to contribute to the understanding of these unique phenomena. O. Shaul et al, *Regulation of Cell Division in Arabidopsis, Critical Reviews in Plant Sciences,* 15(2): 97–112 (1996).

Current transformation technology provides an opportunity to engineer plants with desired traits. Major advances in plant transformation have occurred over the last few years. However, in many major crop plants, serious genotype limitations still exist. Transformation of some agronomically important crop plants continues to be both difficult and time consuming.

For example, it is difficult to obtain a culture response from some maize varieties. Typically, a suitable culture response has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be introduced into and evaluated directly in commercial hybrids.

There is evidence to suggest that cells must be dividing for transformation to occur. It has also been observed that dividing cells represent only a fraction of cells that transiently express a transgene. Furthermore, the presence of damaged DNA in non-plant systems (similar to DNA introduced by particle gun or other physical means) has been well documented to rapidly induce cell cycle arrest (W. Siede, Cell cycle affest in response to DNA damage: lessons from yeast, *Mutation Res.* 337(2:73–84). Methods for increasing the number of dividing cells would therefore provide valuable tools for increasing transformation efficiency.

Current methods for genetic engineering in maize require a specific cell type as the recipient of new DNA. These cells are found in relatively undifferentiated, rapidly growing meristems, in callus, in suspension cultures, or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells.

Exacerbating this problem, the trauma that accompanies DNA introduction directs recipient cells into cell cycle arrest and accumulating evidence suggests that many of these cells are directed into apoptosis or programmed cell death. (Reference Bowen et al., Tucson International Mol. Biol. Meetings). Therefore it would be desirable to provide improved methods capable of increasing transformation efficiency in a number of cell types.

In spite of increases in yield and harvested area worldwide, it is predicted that over the next ten years, meeting the demand for corn will require an additional 20% increase over current production (Dowswell, C. R., Paliwal, R. L., Cantrell, R. P. 1996. Maize in the Third World, Westview Press, Boulder, Co.).

The components most often associated with maize productivity are grain yield or whole-plant harvest for animal feed (in the forms of silage, fodder, or stover). Thus the relative growth of the vegetative or reproductive organs might be preferred, depending on the ultimate use of the crop. Whether the whole plant or the ear are harvested, overall yield will depend strongly on vigor and growth rate. It would therefore be valuable to develop new methods that contribute to the increase in crop yield.

SUMMARY OF THE INVENTION

It is an object of the present invention to provide methods for modulating DNA replication in a transgenic plant.

It is another object of the present invention to provide a method for increasing the number of cells undergoing cell division.

It is another object of the present invention to provide a method for increasing crop yield.

It is another object of the present invention to provide a method for improving transformation frequencies.

It is another object of the present invention to provide a method for improving transformation efficiency in cells from various sources.

It is another object of the present invention to provide a method for providing a positive growth advantage in a plant.

Therefore, in one aspect, the present invention provides a method for increasing transformation frequencies comprising introducing into a target cell a viral replicase polynucleotide operably linked to a promoter driving expression in the target cell or introducing a viral replicase polypeptide.

In another aspect the present invention provides a method for increasing crop yield comprising introducing into a plant cell an isolated viral replicase polynucleotide operably linked to a promoter driving expression in the plant cell.

In another aspect the invention provides a method for providing a positive growth advantage in a target cell comprising introducing into the target cell an isolated viral replicase polynucleotide operably linked to a promoter driving expression in the target cell.

In another aspect the invention provides a method for modulating cell division of target cells comprising introducing into the target cell an isolated viral replicase polynucleotide in sense or antisense orientation operably linked to a promoter driving expression in the target cell or introducing an isolated viral replicase polypeptide.

In another aspect the invention provides a method for transiently modulating cell division of target cells comprising introducing into the target cells an isolated viral replicase polynucleotide in sense or antisense orientation operably linked to a promoter driving expression in the target cells, an isolated viral replicase polypeptide, or an antibody directed against a viral replicase polypeptide.

In another aspect the invention provides a method for providing a means of positive selection comprising (a) introducing into a target cell an isolated viral replicase polynucleotide operably linked to a promoter driving expression in the target cell or an isolated viral replicase polypeptide and (b) selecting for cells exhibiting positive growth advantage.

DETAILED DESCRIPTION OF THE INVENTION

BRIEF DESCRIPTION OF THE DRAWINGS

The file of this patent contains at least one color photograph. Copies of this patent with color photographs will be provided by the Patent and Trademark Office upon request and payment of a fee.

DEFINITIONS

Figure 1A:
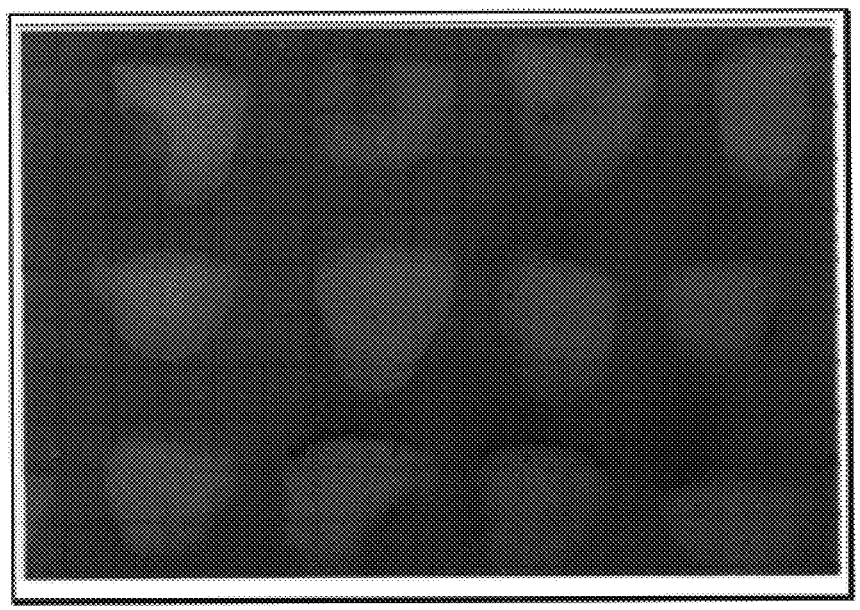
FIG. 1: Comparison of transient GUS expression with and without a Rep-expression cassette.
Figure 1B:
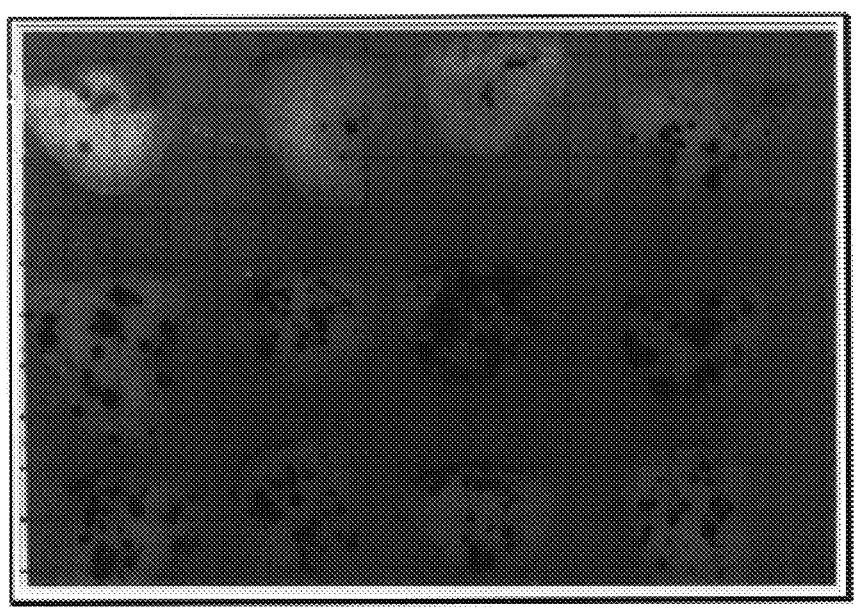
Figure 2A:
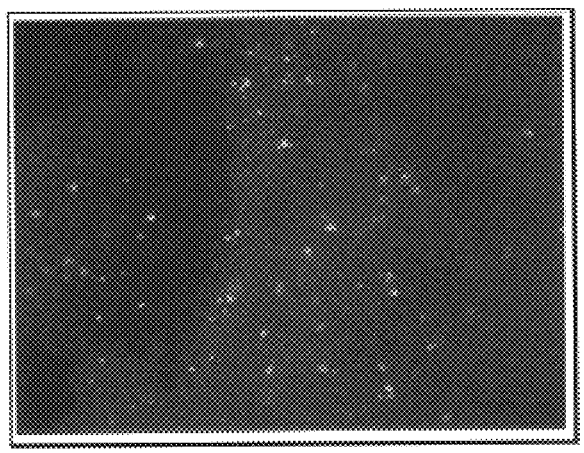
FIG. 2: Micrograph comparison of GFP fluorescence in cells bombarded with and without a Rep-expression cassette.
Figure 2B:
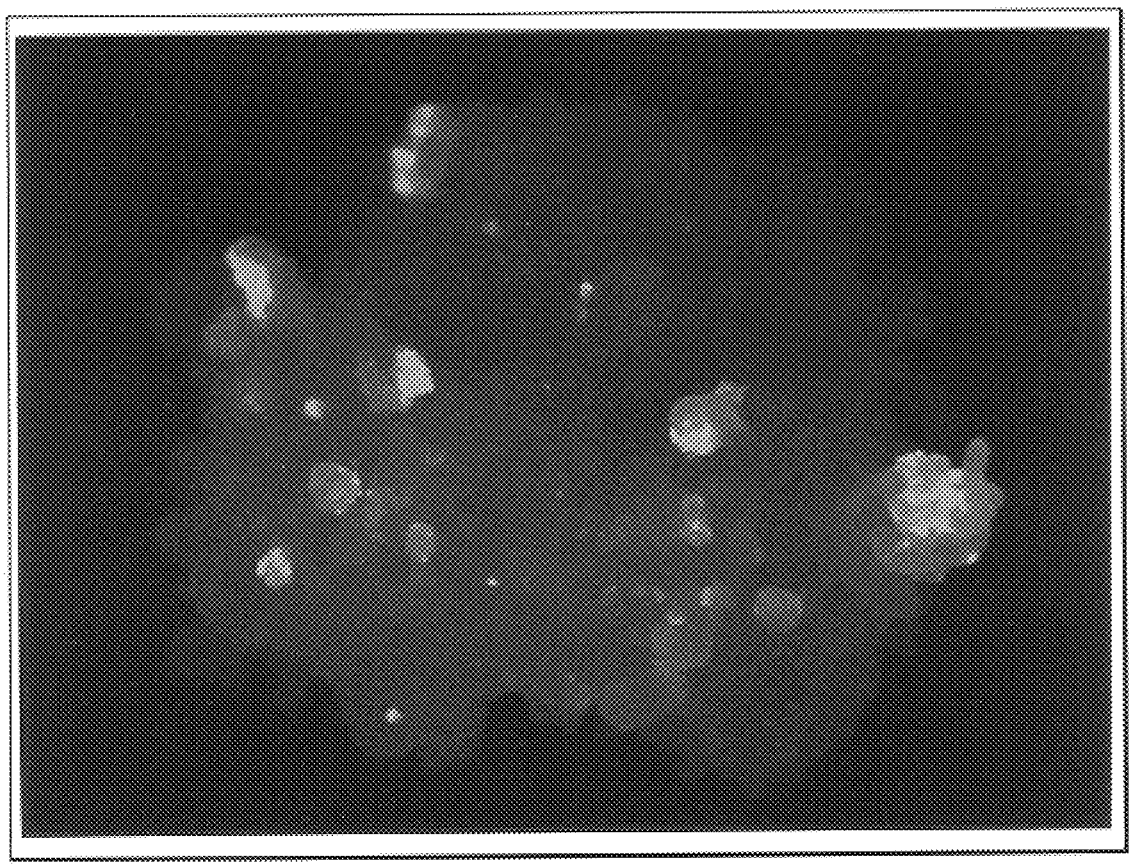
Figure 3A:
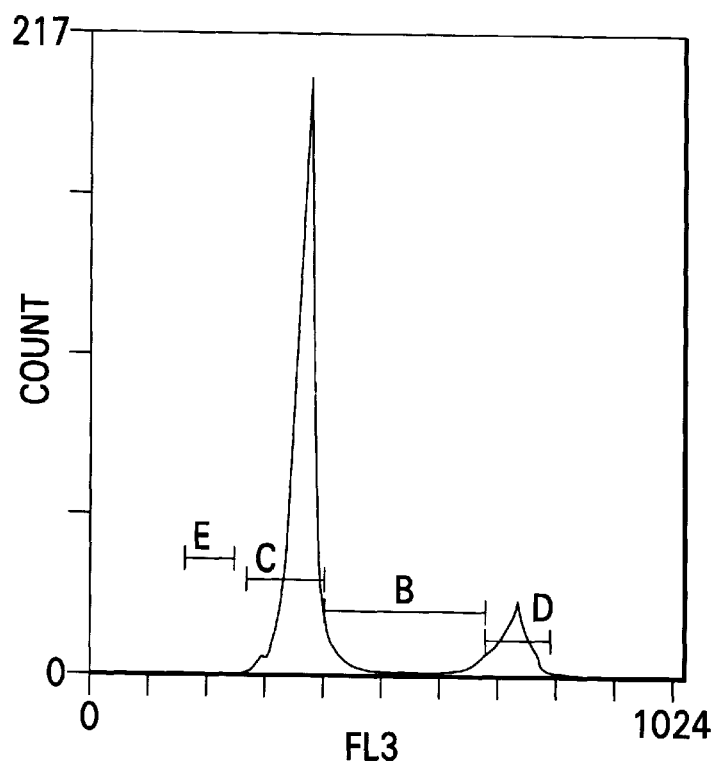
FIG. 3: Comparison of cell cycle profile in callus transformed with and without a Rep-expression cassette.
Figure 3B:
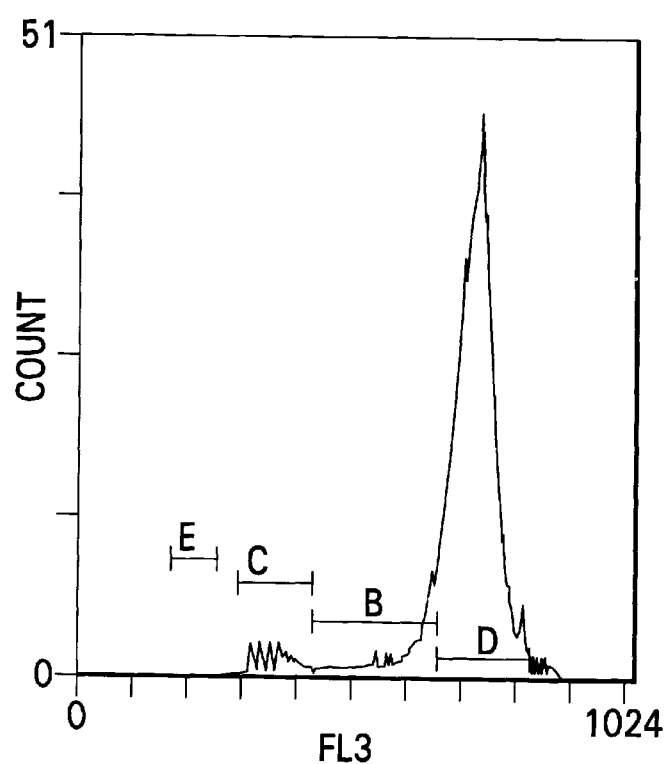

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "polypeptide" and "protein" are used interchangeably and mean proteins, protein fragments, modified proteins, amino acid sequences and synthetic amino acid sequences. The polypeptide can be glycosylated or not.

As used here, "polynucleotide" and "nucleic acid" are used interchangeably. A polynucleotide can be full-length or a fragment and includes polynucleotides that have been modified for stability. Unless otherwise indicated, the term includes reference to a specific sequence or its complement.

As used herein, "functional variant" or "functional derivative" or "functional fragment" are used interchangeably. As applied to polypeptides, the functional variant or derivative is a fragment, a modified polypeptide, or a synthetic polypeptide that stimulates DNA replication in a manner similar to the wild-type gene products, Rep and RepA.

As used herein, "viral replicase polypeptides" refers to polypeptides capable of stimulating DNA replication. The polypeptides are intended to include functional variants, fragments, and derivatives. The polypeptides exhibit the function of binding to the family of retinoblastoma (Rb) proteins, or Rb-associated proteins, or functional Rb homologs. The polypeptides include functional variants or derivatives of viral replicase proteins, and/or functional homologues. The polypeptides include proteins encoded by genes in the viral genome that are commonly referred to as "replication proteins", "replication associated proteins", or "replication initiation proteins". The polypeptide includes proteins from viruses in which all the "replication associated" or "replication" functions are encoded as a single protein, and those in which these functions are carried out by more than one protein, irrespective of whether proper or "inappropriate" splicing has occurred prior to translation (thus including both the polypeptide encoded by the C1 Open Reading Frame, and the polypeptide encoded by the C1–C2 fusion or properly spliced C1–C2).

As used herein, "viral replicase polynucleotide" refers to polynucleotides coding for a viral replicase polypeptide, including functional variants, derivatives, fragments, or functional homologs of characterized viral replicase polynucleotides.

As used herein, "plant" includes but is not limited to plant cells, plant tissue and plant seeds.

The present invention provides novel methods of using viral replicase polypeptides and polynucleotides. Included are methods for increasing transformation frequencies, increasing crop yield, providing a positive growth advantage, modulating cell division, transiently modulating cell division, and for providing a means of positive selection.

Viral replicase polynucleotides, functional variants and/or functional homologs from any virus can be used in the methods of the invention as long as the expressed polypeptides exhibit Rb binding function, and/or stimulates DNA replication.

Examples of suitable plant viruses include wheat dwarf virus, maize streak virus, tobacco yellow dwarf virus, tomato golden mosaic virus, abutilon mosaic virus, cassava mosaic virus, beet curly top virus, bean dwarf mosaic virus, bean golden mosaic virus, chloris striate mosaic virus, digitaria streak virus, miscanthus streak virus, maize streak virus, panicum streak virus, potato yellow mosaic virus, squash leaf curl virus, sugarcane streak virus, tomato golden mosaic virus, tomato leaf curl virus, tomato mottle virus, tobacco yellow dwarf virus, tomato yellow leaf curl virus, African cassava mosaic virus, and the bean yellow dwarf virus.

Other viral proteins that bind Rb-related peptides include the large-T antigen from SV40, adenovirus type 5 E1A protein, and human papilloma virus type 16—E7. Replicase from the wheat dwarf virus has been sequenced and functionally characterized and is therefore preferred. Replicase binds to a well-characterized binding motif on the Rb protein (Xie et al, The EMBO Journal Vol. 14 no.16 pp. 4073–4082, 1995; Orozco et al, Journal of Biological Chemistry, Vol. 272, No. 15, pp. 9840–9846, 1997; Timmermans et al., Annual Review Plant Physiology. Plant Mol. Biol, 45:79–112, 1994; Stanley, Genetics and Development 3:91–96, 1996; Davies et al., *Geminivirus Genomes,* Chapter 2, and Gutierrez, Plant Biology 1:492–497, 1998). The disclosures of these items are incorporated herein by reference.

Viral replicase polynucleotides useful in the present invention can be obtained using (a) standard recombinant methods, (b) synthetic techniques, or combinations thereof.

Viral replicase polynucleotides and functional variants useful in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

Variants of the nucleic acids can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical approach,* (IRL Press, 1991). Thus, the present invention also encompasses DNA molecules comprising nucleotide sequences that have substantial sequence similarity with the inventive sequences. Conservatively modified variants are preferred.

Nucleic acids produced by sequence shuffling of viral replicase polynucleotides can also be used. Sequence shuffling is described in PCT publication No. 96/19256. See also, Zhang, J.-H., et al. *Proc. Natl. Acad. Sci. USA* 94:4504–4509 (1997).

Also useful are 5' and/or 3' UTR regions for modulation of translation of heterologous coding sequences. Positive sequence motifs include translational initiation consensus sequences (Kozak, *Nucleic Acids Res.*15:8125 (1987)) and the 7-methylguanosine cap structure (Drummond et al, Nucleic Acids Res. 13:7375 (1985)). Negative elements include stable intramolecular 5' UTR stem-loop structures (Muesing et al., *Cell* 48:691 (1987)) and AUG sequences or short reading frames 5' of the appropriate AUG in the 5' UTR (Kozak, supra, Rao et al., *Mol. and Cell. Biol.* 8:284 (1988)).

Further, the polypeptide-encoding segments of the polynucleotides can be modified to alter codon usage. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.).

For example, the polynucleotides can be optimized for enhanced or suppressed expression in plants. See, for example, EPA0359472; WO91/16432; Perlak et al. (1991) *Proc. Natl. Acad. Sci. USA* 88:3324–3328; and Murray et al. (1989) *Nucleic Acids Res.* 17:477–498. In this manner, the genes can be synthesized utilizing species-preferred codons. See, for example, Murray et al. (1989) *Nucleic Acids Res.* 17:477–498, the disclosure of which is incorporated herein by reference.

The nucleic acids may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

The polynucleotides can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

To construct genomic libraries, large segments of genomic DNA are generated by random fragmentation. Examples of appropriate molecular biological techniques and instructions are found in Sambrook, et al., *Molecular Cloning: A Laboratory Manual,* 2nd Ed., Cold Spring Harbor Laboratory Vols. 1–3 (1989), Methods in Enzymology, Vol. 152: *Guide to Molecular Cloning Techniques,* Berger and Kimmel, Eds., San Diego: Academic Press, Inc. (1987), *Current Protocols in Molecular Biology,* Ausubel, et al., Eds., Greene Publishing and Wiley-Interscience, New York (1995); *Plant Molecular Biology. A Laboratory Manual,* Clark, Ed., Springer-Verlag, Berlin (1997). Kits for construction of genomic libraries are also commercially available.

The genomic library can be screened using a probe based upon the sequence of a nucleic acid used in the present invention. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Preferably the hybridization is conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C.

An extensive guide to the hybridization of nucleic acids is found in Tijssen, *Laboratory Techniques in Biochemistry and Molecular Biology—Hybridization with Nucleic Acid Probes,* Part I, Chapter 2 *"Overview of principles of hybridization and the strategy of nucleic acid probe assays",* Elsevier, New York (1993); and *Current Protocols in Molecular Biology,* Chapter 2, Ausubel, et al., Eds., Greene Publishing and Wiley-lnterscience, New York (1995). Often, cDNA libraries will be normalized to increase the representation of relatively rare cDNAs.

The nucleic acids can be amplified from nucleic acid samples using amplification techniques. For instance, polymerase chain reaction (PCR) technology can be used to amplify the sequences of polynucleotides of the present invention and related genes directly from genomic DNA or libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997).

The nucleic acids can also be prepared by direct chemical synthesis by methods such as the phosphotriester method of Narang et al, *Meth. Enzymol.* 68: 90–99 (1979); the phosphodiester method of Brown et al, *Meth. Enzymol.* 68: 109–151 (1979); the diethylphosphoramidite method of Beaucage et al., *Tetra. Left.* 22: 1859–1862 (1981); the solid phase phosphoramidite triester method described by Beaucage and Caruthers, *Tetra. Lefts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066.

Expression cassettes comprising the isolated viral replicase nucleic acids are also provided. An expression cassette will typically comprise a polynucleotide operably linked to transcriptional initiation regulatory sequences that will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook, et al.; *Molecular Cloning: A Laboratory Manual;* Cold Spring Harbor, New York; (1989); Gelvin, et al.; *Plant Molecular Biology Manual;* (1990); *Plant Biotechnology: Commercial Prospects and Problems,* eds. Prakash, et al.; Oxford & IBH Publishing Co.; New Delhi, India; (1993); and Heslot, et al.; *Molecular Biology and Genetic Engineering of Yeasts;* CRC Press, Inc., USA; (1992); each incorporated herein in its entirety by reference.

For example, plant expression cassettes may include (1) a viral replicase nucleic acid under the transcriptional control of 5' and 3' regulatory sequences and (2) a dominant selectable marker. Such plant expression cassettes may also contain, if desired, a promoter regulatory region (e.g., one conferring inducible, constitutive, environmentally- or developmentally-regulated, or cell- or tissue-specific/ selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens,* the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21), 6426 (1990). See the following site relating to the waxy promoter: Kloesgen, R. B., Gierl, A., Schwarz-Sommer, Z S. and Saedler, H., Molecular analysis of the waxy locus of *Zea mays, Mol. Gen. Genet.* 203, 237–244 (1986). Promoters that express in the embryo, pericarp, and endosperm are disclosed in U.S. applications Ser. No. 60/097,233 filed Aug. 20, 1998 and No. 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8: 4395 . 4405 (1988); Callis et al., *Genes Dev.* 1: 1183–1200 (1987). Use of maize introns Adh1-S intron 1, 2, and 6, the Bronze-1 intron are known in the art. See generally, *The Maize Handbook,* Chapter 116, Freeling and Walbot, Eds., Springer, New York (1994).

The vector comprising the polynucleotide sequences useful in the present invention will typically comprise a marker gene that confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253–277 (1987). Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.). A variety of plant viruses that can be employed as vectors are known in the art and include cauliflower mosaic virus (CaMV), geminivirus, brome mosaic virus, and tobacco mosaic virus.

The viral replicase polynucleotide can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Nat'l. Acad. Sci. (USA)* 85: 8805–8809 (1988); and Hiatt et al., U.S. Pat. No. 4,801,340.

Another method of suppression is sense suppression. For an example of the use of this method to modulate expression of endogenous genes see, Napoli et al., *The Plant Cell* 2: 279–289 (1990) and U.S. Pat. No. 5,034,323. Another method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al, *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins useful in the present invention include proteins derived from the native protein by deletion (so-called truncation), addition or substitution of one or more amino acids at one or more sites in the native protein. In constructing variants of the proteins of interest, modifications will be made such that variants continue to possess the desired activity.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning*: A Laboratory Manual (Cold Spring Harbor, New York); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The methods of the present invention can be used with any cell such as bacteria, yeast, insect, mammalian, or preferably plant cells. The transformed cells produce viral replicase protein.

Typically, an intermediate host cell will be used in the practice of this invention to increase the copy number of the cloning vector. With an increased copy number, the vector containing the nucleic acid of interest can be isolated in significant quantities for introduction into the desired plant cells. Host cells that can be used in the practice of this invention include prokaryotes, including bacterial hosts such as *Eschericia coli, Salmonella typhimurium,* and *Serratia marcescens*. Eukaryotic hosts such as yeast or filamentous fungi may also be used in this invention. It preferred to use plant promoters that do not cause expression of the polypeptide in bacteria.

Commonly used prokaryotic control sequences include promoters such as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva, et al., Gene 22: 229–235 (1983); Mosbach, et al., *Nature* 302: 543–545 (1983)).

In some aspects of the invention, viral replicase proteins are introduced into a cell to increase cell division. Synthesis of heterologous proteins in yeast is well known. See Sherman, F., et al, *Methods in Yeast Genetics*, Cold Spring Harbor Laboratory (1982). Two widely utilized yeast for production of eukaryotic proteins are *Saccharomyces cerevisiae* and *Pichia pastors*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The protein can be isolated from yeast by lysing the cells and applying standard protein isolation techniques to the lysates. The monitoring of the purification process can be accomplished by using Western blot techniques or radioimmunoassay of other standard immunoassay techniques.

The proteins useful in the present invention can also be constructed using non-cellular synthetic methods. Techniques for solid phase synthesis are described by Barany and Merrifield, Solid-Phase Peptide Synthesis, pp. 3–284 in *The Peptides: Analysis, Synthesis, Biology.* Vol. 2: *Special Methods in Peptide Synthesis,* Part A.; Merrifield, et al., *J. Am. Chem. Soc.* 85: 2149–2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

The proteins useful in this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, Guide to Protein Purification, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art, for example, radioimmunoassays, Western blotting techniques or immunoprecipitation.

Expressing viral replicase polypeptides is expected to provide a positive growth advantage and increase crop yield.

In a preferred embodiment, the invention can be practiced in a wide range of plants such as monocots and dicots. In a especially preferred embodiment, the methods of the present invention are employed in corn, soybean, sunflower, safflower, potato, tomato, sorghum, canola, wheat, alfalfa, cotton, rice, barley and millet.

The method of transformation/transfection is not critical to the invention; various methods of transformation or transfection are currently available. As newer methods are available to transform host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide useful in the present invention, for example a cDNA, RNA or a genomic sequence, will be used to construct an expression cassette that can be introduced into the desired plant. Isolated nucleic acid acids of the present invention can be introduced into plants according to techniques known in the art. Generally, expression cassettes as described above and suitable for transformation of plant cells are prepared.

Methods for transforming various host cells are disclosed in Klein et al. "Transformation of microbes, plants and animals by particle bombardment", Bio/Technol. New York, N.Y., Nature Publishing Company, March 1992, v. 10 (3) pp. 286–291.

Techniques for transforming a wide variety of higher plant species are well known and described in the technical, scientific, and patent literature. See, for example, Weising et al, *Ann. Rev. Genet.* 22: 421–477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al, *Embo J.* 3: 2717–2722 (1984). Electroporation techniques are described in Fromm et al., *Proc. Natl. Acad. Sci.* 82: 5824 (1985). Ballistic transformation techniques are described in Klein et al, *Nature* 327: 70–73 (1987).

*Agrobacterium tumefaciens*-meditated transformation techniques are well described in the scientific literature. See, for example Horsch et al, *Science* 233: 496–498 (1984), and Fraley et al., *Proc. Natl. Acad. Sci.* 80: 4803 (1983). For instance, Agrobacterium transformation of maize is described in U.S. Pat. No. 5,550,318.

Other methods of transformation include (1) *Agrobacterium rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25: 1353, 1984), (3) the vortexing method (see, e.g., Kindle, Proc. *Natl. Acad. Sci., USA* 87: 1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding nucleic acids can be obtained by injection of the DNA into reproductive organs of a plant as described by Pena et al., Nature, 325.:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al, *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al, *Protoplasts Isolation and Culture, Handbook of Plant Cell Culture,* Macmillan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by Agrobacterium can be achieved as described by Horsch et al., *Science,* 227:1229–1231 (1985) and Fraley et al., *Proc. Natl. Acad. Sci. U.S.A.,* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook,* Freeling and Walbot, Eds., Springer, New York (1994); *Corn and Corn Improvement,* $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated viral replicase nucleic acid. Progeny and variants, and mutants of the regenerated plants are also included within the scope of the invention, provided that these parts comprise the introduced nucleic acid sequences.

Transgenic plants expressing a selectable marker can be screened for transmission of the viral replicase nucleic acid, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Plants that can be used in the method of the invention vary broadly and include monocotyledonous and dicotyledonous plants. Preferred plants include corn, soybean, sunflower, sorghum, canola, wheat, alfalfa, cotton, rice, barley, potato, tomato, and millet.

Seeds derived from plants regenerated from transformed plant cells, plant parts or plant tissues, or progeny derived from the regenerated transformed plants, may be used directly as feed or food, or further processing may occur.

Expression of the viral replicase nucleic acids in plants, such as maize, is expected to enhance growth and biomass accumulation. Other more specialized applications exist for these nucleic acids at the whole plant level.

The present invention will be further described by reference to the following detailed examples.

It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES

Example 1

Replicase Constructs

The replicase gene was obtained from Joachim Messing in the vector pWI-11, and was re-designated P100. Using P100 as the source, the replicase structural gene was cloned into an intermediate vector containing the 35S promoter and a 35S 3' sequence (for expression studies in dicotyledonous species, such as tobacco; designated P101 made in the Larkins Lab, Univ. of Arizona). From this intermediate plasmid, the RepA structural gene and the 35S 3' sequence were excised using the restriction enzyme Ncol and PstI, and cloned into P101 (gamma zein promoter::uidA::Gamma zein 3' region; after the removal of the GUS structural gene from P101 using Ncol/PstI). This resulted in a final construct containing an expression cassette with a maize gamma zein promoter sequence (GZ), the RepA coding sequence, a 35S terminator and a gamma zein 3' sequence (GZ'). Thus, the expression cassette had the configuration GZ::RepA::35S::GZ'P102.

A derivative of the pWI-11 vector, with both iudA (encoding GUS expression) and rep gene expression being driven by the bi-directional promoter elements in the WDV long intergenic region (WDV-LIR) was also provided by the Messing lab (pWI-GUS).

Example 2

Replicase Results in Increased Transient Expression of Co-delivered Transgenes The plasmids listed in Table I below were used to evaluate the influence of Rep on transient expression of co-delivered transgenes. The SuperMAS promoter is that described by Ni et al, 1996, Sequence-specific interactions of wound-inducible nuclear factors with mannopine synthase 2' promoter wound responsive elements, Plant Mol. biol. 30:77–96. The visible marker genes, GUS (b-glucoronidase; Jefferson R. A., Plant Mol. Biol. Rep. 5:387, 1987) and GFP (green fluorescent protein; Chalfie et al., Science 263:802, 1994) have been described, as has the maize-optimized GFP (GFPm; see copending U.S. patent application WO 97/41228). The Ubiquitin promoter has been described (Christensen et al., Plant Mol. Biol. 12: 619–632 (1989) and Christensen et al., Plant Mol. Biol. 18: 675–689 (1992), as have the pinII (An et al., 1989, Plant Cell 1: 115–122) and 35S (OdeII et al., 1985, Nature 313: 810–812) 3' regions used in these expression cassettes.

TABLE I

Constructs used to evaluate the effect of replicase expression on transient expression of co-delivered transgenes.

| Plasmid | Description |
| --- | --- |
| P103 | SuperMAS::GUS::pinII 3' region |
| P104 | UBI::moPAT::CaMV35S 3' region |
| P105 | UBI::GFPm::pinII |
| P100 | WDV-LIR promoter::replicase |

GFP Expression in Maize

Transformation of the Rep plasmid DNA, P100, into the Pioneer Hi-Bred Int'l. Inc. proprietary inbred, N38, followed a well-established bombardment transformation protocol used for introducing DNA into the scutellum of immature maize embryos (Songstad, D. D. et al, In Vitro Cell Dev. Biol. Plant 32:179–183, 1996). It is noted that the any suitable method of transformation can be used, such as Agrobacterium-mediated transformation and many other methods. Cells were transformed by culturing maize immature embryos (approximately 1–1.5 mm in length) onto medium containing N6 salts, Erikkson's vitamins, 0.69 g/l proline, 2 mg/l 2,4-D and 3% sucrose. After 4–5 days of incubation in the dark at 28° C., embryos were removed from the first medium and cultured onto similar medium containing 12% sucrose. Embryos were allowed to acclimate to this medium for 3 h prior to transformation. The scutellar surface of the immature embryos was targeted using particle bombardment with either a UBI::GFPm::pinII plasmid+a UBI::maize-optimized PAT::pinII plasmid (P105, control treatment) or with a combination of the UBI::GFP-m::pinII plasmid P104+ the replicase plasmidP100. Embryos were transformed using the PDS-1000 Helium Gun from Bio-Rad at one shot per sample using 650PSI rupture disks. DNA delivered per shot averaged at 0.0667 ug. An equal number of embryos per ear were bombarded with either the control DNA mixture or the Rep/GFP DNA mixture. Following bombardment, all embryos were maintained on standard maize culture medium (N6 salts, Erikkson's vitamins, 0.69 g/l proline, 2 mg/l 2,4-D, 3% sucrose) for 2–3 days and then evaluated for transient GFP expression.

In both experiments, greater numbers of cells on the scutellar surface transiently expressed GFP in the replicase-containing treatment. In experiment #1 with genotype N38, a mean of only 12 cells per embryo transiently expressed GFP in the treatment without replicase, while in the replicase-treated embryos the mean number of GFP-expressing cells was almost 20-fold greater (see Table II below). In the second experiment (Table III below), transient GFP expression in the replicase-containing treatments was approximately 6.5-fold greater than in the control treatments (no replicase).

TABLE II

Maize Experiment #1: Transient GFP expression is stimulated by Replicase

| Genotype & Explant | Treatment (plasmids used) | GFP-expressing cells/embryo* | Mean |
| --- | --- | --- | --- |
| N38 immature embryos | P104, P100 | 165, 290, 413, 149, 148 | 233 |
| N38 immature embryos | P104, P105 | 1, 22, 13 | 12 |

TABLE III

Maize Experiment #2: Transient GFP expression Is stimulated by Replicase

| Genotype & Explant | Treatment (plasmids used) | GFP-expressing cells/embryo* | Mean |
| --- | --- | --- | --- |
| N38 immature embryos | P104, P100 (insert) | 1122, 108, 285, 27, 249 | 358 |
| N38 immature embryos | P104, P105 | 240, 10, 11, 0, 0 | 52 |

*the number of GFP-expressing cells per embryo was averaged across all 25 embryos on the plate.

Soybean

Tissue was excised from coytledons and placed on MS-based medium. A mixture of plasmid DNA, containing equal amounts of a SuperMas::GUS::pinII plasmid (P103) and the WDV-LIR::replicase plasmid (P100) was delivered into cells on the surface of the cotlyledon explants using particle-mediated delivery similar to that described for maize above. As a control, SuperMas::GUS::pinII plasmid (P103)+UBI::moPAT::CaMV35S (P105) was introduced into the same target cells using an equal number of cotyledonary tissue pieces.

In the replicase-treatment, greater numbers of transiently expressing cells were observed on the cotyledon after GUS staining (see FIG. I). In addition, for cells exhibiting transient gene expression, the level of expression as judged by relative intensity of histochemical staining appeared greater in replicase-treated tissues (as compared to controls).

Example 3

RepA Increases Growth Rates in Early-developing Stable Maize Transformants

Transformation of the RepA plasmid DNA (P102), P102in Hi-II followed the standard Hi-II bombardment transformation protocol (Songstad D. D. et al, In Vitro Cell Dev. Biol. Plant 32:179–183, 1996). Cells were transformed by culturing maize immature embryos (approximately 1–1.5 mm in length) onto 560P medium containing N6 salts, Erikkson's vitamins, 0,69 g/l proline, 2 mg/l 2,4-D and 3% sucrose. After 4–5 days of incubation in the dark at 28° C., embryos were removed from 560P medium and cultured, scutellum up, onto 560Y medium which is equivalent to 560P but contains 12% sucrose. Embryos were allowed to acclimate to this medium for 3 h prior to transformation. The scutellar surface of the immature embryos was targeted using particle bombardment with either a UBI::moPAT~GFPm::pinII plasmid (P106 alone as a control treatment) or with a combination of the UBI::moPAT~GFPm::pinII plasmid (P106)+ the GZ::RepA::35S:GZ' plasmid (P102). Embryos were transformed using the PDS-1000 Helium Gun from Bio-Rad at one shot per sample using 650PSI rupture disks. DNA delivered per shot averaged at 0.0667 ug. An equal number of embryos per ear were bombarded with either the control DNA (PAT~GFP) or the RepA/PAT~GFP DNA mixture. Following bombardment, all embryos were maintained on 560L medium (N6 salts, Eriksson's vitamins, 0.5 mg/i thiamine, 20 g/l sucrose, 1 mg/l 2,4-D, 2.88 g/l proline, 2.0 g/l gelrite, and 8.5 mg/l silver nitrate). After 2–7 days post-bombardment, all the embryos from both treatments were transferred onto N6-based medium containing 3 mg/l bialaphos Pioneer 560P medium described above, with no proline and with 3 mg/l bialaphos). Plates were maintained at 28° C. in the dark and were observed for colony recovery with transfers to fresh medium occurring every two weeks. Two weeks after DNA delivery, the newly-forming callus was examined using epifluorescence under the dissecting microscope (using commercially-available filter combinations for GFP excitation and emission).

At 2 weeks post-bombardment, numerous cells on the surface of the scutellar-derived tissue were expressing GFP in the control treatment (no RepA), but all expressing foci consisted of single cell. No multicellular GFP-expressing clusters were observed in the control. At this same time-point, 2-weeks after DNA-delivery, the same sprinkling of single-celled GFP-expressing foci were observed on the surface of the tissue that had received the RepA/PAT~GFP mixture. However, numerous macroscopic GFP-expressing multicellular clusters were also apparent (see FIG. II). Many embryos were observed with multiple transgenic microcalli developing on the surface, with as many as 7 apparently-independent transformants beginning to grow from a single embryo (this has never been reported before for particle bombardment of maize).

After 3 weeks, GFP-expressing single cells could still be observed in both treatments, although the frequency had declined. In the control treatment, a solitary GFP-expressing multicellular colony we observed to be developing on one embryo (out of 50 total). In the RepA-treated embryos, the growth rate of the developing transgenic calli continued to be very rapid. Many of the multiple colonies apparently growing from single embryos were already in danger of co-mingling by growing together into a single mass. Many colonies were picked off the embryos to grow them separately. At 5 weeks post-bombardment, many RepA colonies continued to grow rapidly (some may have been too small to survive independently). While growing rapidly, these RepA-treated transgenic calli maintain a healthy embryogenic character.

Example 4

RepA Increases Cell Division Rates in Tobacco Suspension Culture Cells

For tobacco BY-2 suspension culture cells, the following construct was used; 35S promoter::RepA::35S 3' region (P101). Suspension cells were grown in a medium comprised of Murashige and Skoog salts (Life Technologies, Inc., Grand Island, N.Y.), 100 mg/l inositol, 1 mg/l thiamine, 180 mg/l KH2PO4, 30 g/l sucrose, and 2 mg/l 2,4-D, subcultured every 7–10 days, and grown on a gyratory shaker at 150 RPM, 24° C. in the dark. Three days after subculturing, cells were pipetted onto solidified agar medium for bombardment, and left in the dark for 24 hours. Bombardment was performed using a BioRad PDS-1000, using helium at 650 PSI and 25 inches Hg, with 8 cm distance between the stopping plate and petri dish. All cells were shot once with 500 ng gold and 0.5 $\mu$g DNA. All the treated cells received a plasmid containing a 35S::GFP::35S expression cassette (P108), with half receiving an additional plasmid containing the 35S::RepA::35S cassette. After bombardment, the cells were monitored for GFP expression and cell division.

After 24 hours, GFP-expressing cells were scored as non-dividing (single fluorescent cells) or as having divided during the intervening 24-hour period (i.e. GFP-expressing doublets with the characteristic newly-formed division plate between the two fluorescent daughter cells). For the control treatment (GFP alone), 37.5% (with a standard error of 1.8, calculated for three replicates) of the total number of GFP-expressing cells had undergone division during this period. In the treatment where GFP+RepA expression cassettes were introduced simultaneously, the percentage of GFP-expressing cells that had undergone division increased substantially to 45.7 (SE=5.7).

Example 5

RepA Increases Maize Transformation Frequency

For transformation experiments, a construct was used in which the RepA coding sequence was cloned into a maize expression cassette (P102, described above). Delivery of the RepA gene in an appropriate plant expression cassette (for example, in a GZ::RepA::35S:GZ-containing plasmid) along with marker gene cassettes was accomplished using particle bombardment. DNA was introduced into maize cells capable of growth on suitable maize culture medium (freshly isolated immature embryos). See Table IV below for treatments. Immature embryos of the Hi-II genotype were used as the target for co-delivery of plasmids. To assess the effect on transgene integration, growth of bialaphos-resistant colonies on selective medium was a reliable assay. Within 1–7 days after DNA introduction, the embryos were moved onto culture medium containing 3 mg/l of the selective agent bialaphos. Embryos, and later callus, were transferred to fresh selection plates every 2 weeks. Four-six weeks after bombardment, bialaphos-resistant calli were scored and transferred to separate plates to prevent mixing of transformants as they continue to grow. Expression of the visible scorable marker (GUS or GFP) was used to confirm transformation. In the RepA-treated embryos, higher numbers of stable transformants were recovered (likely a direct result of increased integration frequencies).

TABLE IV

Experimental design for assessing the influence of RepA expression on recovery of stable maize transformants.

| Experiment # | Control | Treatment |
|---|---|---|
| 1 & 2 | None included in experiment | E35S::bar::pinII + UBI::GUS::pinII + GZ::RepA::35S:GZ' |
| 3 | UBI::PATm-GFPm::pinII | UBI::PATm-GFPm::pinII + GZ::RepA::35S:GZ' |

Experiment #1

This experiment was originally designed to test RepA expression in endosperm. Thus, we used all of the embryos from the available Hi-II ears on this day to introduce RepA along with the marker genes (P107 the construct containing Enhanced-35S promoter::bar::pinII and UBI::GUS::pinII). The frequencies for Hi-II transformation using P107 alone (E35S::bar::pinII+UBI::GUS::pinII) during this period were averaging between 2–3%, providing a good basis of comparison. In this experiment, our transformation frequency with P107+GZ::RepA (P102) was 8.8% (33 transformants/375 starting embryos).

Experiment #2

Again, the original intent of this experiment was to generate endosperm-expressing RepA transformants (not to compare transformation frequencies). As in the first experiment, the observed result was unexpected; transformation frequency using P107+GZ::RepA (P102) was 29.2% (73 transformants/250 starting embryos). This represented approximately a 10-fold increase over the 2–3% transformation frequencies observed in other experiments conducted during this period using similar marker genes (the bar gene to confer bialaphos resistance and GUS as a visible marker).

Experiment #3

In this experiment, numerous ears were used. Immature embryos were isolated from each ear, randomized on plates and then split between each of the two treatments (+/− RepA). This comparison used a total of 725 embryos per treatment, harvested from a total of 29 ears (25 embryos/ear/treatment). Transformation frequencies were calculated on a per-ear basis and then expressed as the mean.

| Treatment | Mean Transformation Frequency (%) | Standard Deviation |
|---|---|---|
| UBI::PATm-GFPm::pinII (Control) | 2.2 | 1.8 |
| UBI::PATm-GFPm::pinII + GZ::RepA:35S:GZ' | 17.0 | 8.5 |

This tightly controlled experiment validated the preliminary results in Experiments #1 & #2. Across many replicates (individual ears harvested on separate dates), the mean frequency for RepA-treated immature embryos was over 7.5-fold greater than for embryos treated solely with the control plasmid. For particle-mediated transformation of Hi-II immature embryos, this is a remarkable improvement in transformation frequency. The calli recovered from the RepA treatments grew vigorously, were embryogenic, and easily regenerated into plants. Plants regenerated to date have appeared phenotypically normal, were both male and female fertile, and transmitted the transgenes (and their expression) to progeny in expected Mendelian ratios.

Example 6

RepA Alters the Cell Cycle Phenotype in Cell Populations from Transgenic Calli

Transformation of Hi-II immature embryos was performed using the prottocol described in Example 3. A mixture of plasmid DNA, containing equal amounts of a E35S::bar::pinII+UBI::GUS::pinII plasmid (P107) and a GZ::RepA35S::GZ' plasmid (P102), was delivered into scutellar cells of the immature embryos using particle-mediated delivery. As a control, E35S::bar::pinII+ UBI::GUS::pinII (P107) plasmid alone was introduced into the same target cells on the surface of the scutellum for an equal number of embryos. One week after particle bombardment, all the embryos from both treatments were transferred onto N6-based medium containing 3 mg/l bialaphos. After 6 weeks, stable transformants were scored, and expression of a second marker gene (GUS) was used to confirm the transgenic nature of the callus. Transgenic callus expressing bar and GUS alone (from the control treatment), or transgenic callus expressing bar, GUS and RepA were used to isolate nuclei. For extraction of nuclei, callus was macerated with a straight-edge razor blade in a buffer consisting of 45 mM $CgCL_2$, 30 mM sodium citrate, 20 mM MOPS buffer, 0.1% v/v Triton X 100. For each callus event sampled, tissue (approximately 1 $cm^3$) was transferred to a Petri dish, and macerated with a small volume of the chopping buffer. The resulting suspension was then passed sequentially through 60 um and 20 um sieves and transferred to a 15 ml centrifuge tube on ice. Tubes were centrifuged at 100 g for 5 minutes at 4° C. The supernatant was decanted, the pellets resuspended in ~750 $\mu$l of staining solution (100 $\mu$g/ml propidium iodide in chopping buffer) and transferred to tubes for analysis in the flow cytometer. Stained nuclei were analyzed on an EPICS-XL-MCL flow cytometer using a 488 nm argon laser for excitation and measuring emission from 500–550 nm. Collecting propidium iodide fluorescence measurements on a per-nucleus basis (equivalent to the DNA content per nucleus) permitted the assessment of cell cycle stages in the callus-cell population.

The cell cycle profile from the control callus was typical of maize callus cell populations, with a predominant G1 peak (approximately 80%), a low percentage of S phase (8%), and a low percentage of G2 (approximately 12%). In a RepA-treated callus transformant, the cell cycle profile was dramatically shifted, with approximately 7% G1, 8% S phase and 85% in the G2 phase (see FIG. III).

Example 7

Transient ReNA Activity Enhances Transformation Frequency

For this specific application (using transient RepA-mediated cell cycle timulation to increase transient integration frequencies), it may be desirable to reduce the likelihood of ectopic stable expression of the RepA gene. Strategies for transient-only expression can be used. This includes delivery of RNA (transcribed from the RepA gene), chemically end-modified DNA expression cassettes that typically will not integrate, or RepA protein along with the transgene cassettes to be integrated to enhance transgene integration by transient stimulation of cell division. Using well-established methods to produce RepA-RNA, this can then be purified and introduced into maize cells using physical methods such as microinjection, bombardment, electroporation or silica fiber methods. For protein delivery, the gene is first expressed in a bacterial or baculoviral system, the protein purified and then introduced into maize cells using physical methods such as microinjection, bombardment, electroporation or silica fiber methods. Alternatively, RepA proteins are delivered from *Agrobacterium tumefaciens* into plant cells in the form of fusions to Agrobacterium virulence proteins. Fusions are constructed between RepA and bacterial virulence proteins such as VirE2, VirD2, or VirF which are known to be delivered directly into plant cells. Fusions are constructed to retain both those properties of bacterial virulence proteins required to mediate delivery into plant cells and the RepA activity required for enhancing transgene integration. This method ensures a high frequency of simultaneous co-delivery of T-DNA and functional RepA protein into the same host cell. The methods above represent various means of using the RepA gene or its encoded product to transiently stimulate DNA replication and cell division, which in turn enhances transgene integration by providing an improved cellular/molecular environment for this event to occur.

Example 8

Altering RepA Expression Stimulates the Cell Cycle and Growth

Based on our observations, expression of RepA genes increases cell division rates. Increases in division rate are assessed in a number of different manners, being reflected in smaller cell size, more rapid incorporation of radiolabeled nucleotides, and faster growth (i.e. more biomass accumulation). Delivery of the RepA in an appropriate plant expression cassette is accomplished through numerous well-established methods for plant cells, including for example particle bombardment, sonication, PEG treatment or electroporation of protoplasts, electroporation of intact tissue, silica-fiber methods, microinjection or Agrobacterium-mediated transformation. The result of RepA gene expression will be to stimulate the G1/S transition and hence cell division, providing the optimal cellular environment for integration of introduced genes (as per Example 1). This will trigger a tissue culture response (cell divisions) in genotypes that typically do not respond to conventional culture techniques, or stimulate growth of transgenic tissue beyond the normal rates observed in wild-type (non-transgenic) tissues. To demonstrate this, the RepA gene is cloned into a cassette with a constitutive promoter (i.e. either a strong maize promoter such as the ubiquitin promoter including the first ubiquitin intron, or a weak constitutive promoter such as nos). Either particle-mediated DNA delivery or Agrobacterium-mediated delivery are used to introduce the GZ::RepA::35S:GZ-containing plasmid along with a UBI::bar::pinII-containing plasmid into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids, and within 1–7 days the embryos are moved onto culture medium containing 3 mg/l of the selective agent bialaphos. Embryos, and later callus, are transferred to fresh selection plates every 2 weeks. After 6–8 weeks, transformed calli are recovered. In treatments where both the bar gene and RepA gene have been transformed into immature embryos, a higher number of growing calli are recovered on the selective medium and callus growth is stimulated (relative to treatments with the bar gene alone). When the RepA gene is introduced without any additional selective marker, transgenic calli can be identified by their ability to grow more rapidly than surrounding wild-type (non-transformed) tissues. Transgenic callus can be verified using PCR and Southern analysis. Northern analysis can also be used to verify which calli are expressing the bar gene, and which are expressing the maize RepA gene at levels above normal wild-type cells (based on hybridization of probes to freshly isolated mRNA population from the cells).

Inducible Expression

The RepA gene can also be cloned into a cassette with an inducible promoter such as the benzenesulfonamide-inducible promoter. The expression vector is co-introduced into plant cells and after selection on bialaphos, the transformed cells are exposed to the safener (inducer). This chemical induction of RepA expression results in stimulated G1/S transition and more rapid cell division. The cells are screened for the presence of RepA RNA by northern, or RT-PCR (using transgene specific probesloligo pairs), for RepA-encoded protein using RepA-specific antibodies in Westerns or using hybridization. Increased DNA replication is detected using BrdU labeling followed by antibody detection of cells that incorporated this thymidine analogue. Likewise, other cell cycle division assays could be employed, as described above.

Example 9

Control of RepA Gene Expression Using Tissue-specific or Cell-specific Promoters Provides a Differential Growth Advantage RepA gene expression using tissue-specific or cell-specific promoters stimulates cell cycle progression in the expressing tissues or cells. For example, using a seed-specific promoter will stimulate cell division rate and result in increased seed biomass. Alternatively, driving RepA expression with an tassel-specific promoter will enhance development of this entire reproductive structure.

Expression of RepA genes in other cell types and/or at different stages of development will similarly stimulate cell division rates. Similar to results observed in Arabidopsis (Doerner et al. Nature Apr. 11, 1996, 380(6574):520–523), root-specific or root-preferred expression of RepA will result in larger roots and faster growth (i.e. more biomass accumulation).

Example 10

Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival. Transformation of an apical initial with a RepA expression cassette under the expression of a promoter active in the apical meristem (either meristem specific or constitutive) would allow the transformed cells to grow faster and displace wildtype initials driving the meristem towards homogeneity and minimizing the chimeric nature of the plant body. To demonstrate this, the RepA gene is cloned into a cassette with a promoter that is active within the meristem (i.e. a promoter active in meristematic cells such as the maize histone, cdc2 or actin promoter). Coleoptilar stage embryos are isolated and plated meristem up on a high sucrose maturation medium (see Lowe et al. Transformation of the maize apical meristem: Transgenic sector reorganization and germline transmission, in "Genetics, Biotechnology and Breeding of Maize and Sorghum", (A. S. Tsaftaris, ed.), Royal Society of Chemistry, Cambridge, UK, pp 94–97, 1997). The RepA expression cassette along with a reporter construct such as Ubi:GUS:pinII can then be co-delivered (preferably 24 hours after isolation) into the exposed apical dome using conventional particle gun transformation protocols. As a control the RepA construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the RepA gene in meristem cells, through stimulation of the G1→S transition, will result in greater integration frequencies and hence more numerous transgenic sectors. Integration and expression of the RepA gene will impart a competitive advantage to expressing cells resulting in a progressive enlargement of the transgenic sector. Due to the enhanced growth rate in RepA-expressing meristem cells, they will supplant wildtype meristem cells as the plant continues to grow. The result will be both enlargement of transgenic sectors within a given cell layer (i.e. periclinal expansion) and into adjacent cell layers (i.e. anticlinal invasions). As an increasingly large proportion of the meristem is occupied by RepA-expressing cells, the frequency of RepA germline inheritance goes up accordingly.

Example 11

Use of Flp/Frt System to Excise the RepA Cassette

In cases where the RepA gene has been integrated and RepA expression is useful in the recovery of maize trangenics, but is ultimately not desired in the final product, the RepA expression cassette (or any portion thereof that is flanked by appropriate FRT recombination sequences) can be excised using FLP-mediated recombination (see copending U.S. patent application Ser. No. 98/24640).

What is claimed is:

1. A method for increasing transformation frequency of a plant cell comprising introducing into a plant cell an isolated plant geminivirus replicase polynucleotide to produce a transformed plant cell, and growing the transformed plant cell under conditions sufficient to express the replicase polynucleotide, wherein the replicase polynucleotide is operably linked to a promoter capable of driving expression in the transformed plant cell.

2. The method of claim 1 further comprising introducing at least one polynucleotide of interest operably linked to a second promoter capable of driving expression in the plant cell.

3. The method of claim 1 further comprising regenerating a plant from the transformed plant cell.

4. A method for increasing crop yield comprising stably transforming a plant cell with an isolated plant geminivirus replicase polynucleotide operably linked to a promoter capable of driving expression in the plant cell, growing the plant cell under conditions sufficient to express the geminivirus polynucleotide, and regenerating a plant having increased yield compared to a corresponding plant that has not been transformed with the geminivirus polynucleotide.

5. The method according to claim 4 further comprising introducing at least one polynucleotide of interest operably linked to a promoter capable of driving expression in the plant cell.

6. The method of claim 4 wherein the promoter is inducible, tissue specific, developmentally regulated, or temporally regulated.

7. A method for providing a positive growth advantage in a plant cell comprising introducing into the plant cell an isolated plant geminivirus replicase polynucleotide operably linked to a promoter capable of driving expression in the plant cell and growing the plant cell under conditions sufficient to express the polynucleotide.

8. The method of claim 7 wherein the promoter is inducible, tissue specific, developmentally regulated, or temporally regulated.

9. A method for providing a means of positive selection comprising introducing into a plant cell an isolated plant geminivirus replicase polynucleotide, growing the cells under conditions sufficient to express the polynucleotide and selecting for cells exhibiting a positive growth advantage.

10. The method of claim 9 further comprising introducing a polynucleotide expressing a screenable marker.

11. The method of claim 1 wherein the polynucleotide encodes a wheat dwarf virus Replicase.

12. The method of claim 1 wherein the plant cell is from a monocot or a dicot plant.

13. The method of claim 12 wherein the plant cell is from corn, soybean, sunflower, sorghum, canola, wheat, alfalfa, cotton, rice, barley, potato, tomato, or millet.

14. The method of claim 4 wherein the polynucleotide encodes a wheat dwarf virus Replicase.

15. The method of claim 4 wherein the plant cell is a monocot or a dicot.

16. The method of claim 15 wherein the plant cell is from corn, soybean, sunflower, sorghum, canola, wheat, alfalfa, cotton, rice, barley, potato, tomato, or millet.

17. The method of claim 7 wherein the polynucleotide encodes a wheat dwarf virus Replicase.

18. The method of claim 7 wherein the plant cell is a monocot or a dicot.

19. The method of claim 18 wherein the plant cell is from corn, soybean, sunflower, sorghum, canola, wheat, alfalfa, cotton, rice, barley, potato, tomato, and millet.

20. The method of claim 9 further comprising introducing at least one polynucleotide of interest operably linked to a second promoter capable of driving expression in the plant cell.

* * * * *

UNITED STATES PATENT AND TRADEMARK OFFICE
CERTIFICATE OF CORRECTION

PATENT NO.    : 6,284,947 B1
DATED         : September 4, 2001
INVENTOR(S)   : William J. Gordon-Kamm et al.

It is certified that error appears in the above-identified patent and that said Letters Patent is hereby corrected as shown below:

<u>Title page,</u>
Item [73], Assignee, should read as follows:
-- [73]   Assignee:  Pioneer Hi-Bred International, Inc.
             Des Moines, IA (US)

**The Arizona Board of Regents Acting
             on behalf of The University of Arizona**
             Tucson, AZ (US) --

Signed and Sealed this

Tenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,284,947 B1
DATED : September 4, 2001
INVENTOR(S) : Gordon-Kamm et al.

It is certified that error appears in the above-identified patent and that said Letters Patent is hereby corrected as shown below:

Column 1,
Line 3, before "TECHNICAL FIELD" insert the following:
-- STATEMENT REGARDING FEDERALLY SPONSORED RESEARCH OR DEVELOPMENT
This invention was made with Government support under Contract No. DE-FG03-95ER20183 awarded by the Department of Energy. The Government has certain rights in this invention. --.

Signed and Sealed this

Twentieth Day of December, 2005

JON W. DUDAS
*Director of the United States Patent and Trademark Office*